(12) United States Patent
De Haan et al.

(10) Patent No.: US 11,326,188 B2
(45) Date of Patent: *May 10, 2022

(54) THERMAL DECOMPOSITION OF MAGNESIUM CHLORIDE

(71) Applicant: PURAC BIOCHEM BV, Gorinchem (NL)

(72) Inventors: André Banier De Haan, Gorinchem (NL); Jeroen Bokhove, Gorinchem (NL); Fesia Lestari Laksmana, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 202 days.

This patent is subject to a terminal disclaimer.

(21) Appl. No.: 16/590,422

(22) Filed: Oct. 2, 2019

(65) Prior Publication Data

US 2020/0032300 A1 Jan. 30, 2020

Related U.S. Application Data

(63) Continuation of application No. 15/129,431, filed as application No. PCT/EP2015/056895 on Mar. 30, 2015.

(30) Foreign Application Priority Data

Apr. 1, 2014 (EP) .................................... 14162999

(51) Int. Cl.
*C12P 7/40* (2006.01)
*C01F 5/10* (2006.01)
*C01B 7/03* (2006.01)

(52) U.S. Cl.
CPC ................ *C12P 7/40* (2013.01); *C01B 7/035* (2013.01); *C01F 5/10* (2013.01)

(58) Field of Classification Search
CPC .............. C01F 5/10; C01B 7/035; C12P 7/40
See application file for complete search history.

(56) References Cited

U.S. PATENT DOCUMENTS

| 1,479,982 A | 1/1924 | Collings et al. |
| 1,874,735 A | 8/1932 | Barstow et al. |
| (Continued) | | |

FOREIGN PATENT DOCUMENTS

| DE | 1102712 B | 3/1961 |
| DE | 28740 A | 5/1964 |
| (Continued) | | |

OTHER PUBLICATIONS

Jun. 19, 2015 International Search Report issued in International Patent Application No. PCT/EP2015/056895.

(Continued)

*Primary Examiner* — Ngoc-Yen Nguyen
(74) *Attorney, Agent, or Firm* — Oliff PLC

(57) ABSTRACT

A method for conversion of magnesium chloride into magnesium oxide and HCl includes the steps of providing a magnesium chloride compound to a thermohydrolysis reactor, the reactor being at a temperature of at least 300° C., withdrawing MgO from the thermohydrolysis reactor in solid form, and withdrawing an HCl containing gas stream from the thermohydrolysis reactor. The magnesium chloride compound provided to the thermohydrolysis reactor may be a solid magnesium chloride compound which comprises at least 60 wt. % of $MgCl_2 \cdot 4H_2O$.

30 Claims, 2 Drawing Sheets

(56) References Cited

U.S. PATENT DOCUMENTS

| | | | |
|---|---|---|---|
| 4,425,314 | A | 1/1984 | Gattys |
| 2009/0110654 | A1 | 4/2009 | Hagemann et al. |
| 2010/0157852 | A1 | 6/2010 | Nelson et al. |
| 2010/0158782 | A1 | 6/2010 | Blencoe |
| 2014/0357877 | A1 | 12/2014 | De Haan et al. |
| 2015/0004663 | A1* | 1/2015 | De Haan .................. C12P 7/56 |
| | | | 435/136 |
| 2016/0369302 | A1* | 12/2016 | De Vries .................. C01B 7/01 |

FOREIGN PATENT DOCUMENTS

| | | |
|---|---|---|
| EP | 0025427 A1 | 3/1981 |
| WO | 00/017378 A2 | 3/2000 |
| WO | 01/030699 A1 | 5/2001 |
| WO | 2013/025106 A1 | 2/2013 |
| WO | 2013/093028 A1 | 6/2013 |
| WO | 2013/117687 A1 | 8/2013 |

OTHER PUBLICATIONS

Jun. 19, 2015 Written Opinion issued in International Patent Application No. PCT/EP2015/056895.
Jul. 23, 2019 Office Action issued in European Patent Application No. 15712655.8.
Hyoung-Choon Eom et al., "Dehydration characteristics of Magnesium Chloride Hydrate", Journal of the Korean Institute of Resources Recycling, vol. 16, No. 5, Oct. 27, 2007 (pp. 8-12).
Dec. 30, 2019 Office Action issued in Brazilian Patent Application No. BR112016021806-0.
Aug. 5, 2021 Office Action issued in U.S. Appl. No. 16/992,828.

* cited by examiner

THERMAL DECOMPOSITION OF MAGNESIUM CHLORIDE

The present application is a continuation application of U.S. application Ser. No. 15/129,431 filed Sep. 27, 2016, which in turn is a U.S. national stage application of PCT/EP2015/056895 filed Mar. 30, 2015. Each of these prior applications is incorporated herein by reference in its entirety.

BACKGROUND

The present invention pertains to a method for conversion of magnesium chloride into magnesium oxide and HCl. The invention also pertains to a method for converting a magnesium chloride solution, and to in integrated process comprising a fermentation step, a separation step, and a step for converting a magnesium chloride solution.

Methods for manufacturing carboxylic acids through fermentation are known in the art. In these methods, the carboxylic acid is often prepared in the form of a salt, e.g. a magnesium salt. Upon recovering the carboxylic acid, salt solutions are obtained, which require further processing.

For example, WO00/17378 describes a method for manufacturing lactic acid, wherein in a fermentation process a magnesium lactate solution is prepared. The magnesium lactate solution is acidified with HCl to yield a solution comprising lactic acid in a magnesium chloride solution. The lactic acid is recovered from the solution. The resulting magnesium chloride solution may be processed by subjecting it to a thermohydrolysis step at a temperature of at least 500° C. to react the magnesium chloride with water to yield magnesium oxide powder and hydrochloric acid. The heat required for the thermohydrolytic reaction is provided by the in situ combustion of fuel.

WO2013/025106 describes a method for manufacturing carboxylic acids through a process comprising the steps of acidifying a magnesium salt of a carboxylic acid with HCl to form an acid and a magnesium chloride solution, and isolating the acid from the solution through precipitation. It is indicated that the magnesium chloride solution may be processed through thermal decomposition.

WO2013/093028 describes a method for manufacturing carboxylic acids through a process comprising the steps of acidifying a magnesium salt of a carboxylic acid with HCl to form an acid and a magnesium chloride solution, and isolating the acid from the solution through extraction followed by back extraction. It is indicated that the magnesium chloride solution may be processed through thermal decomposition.

In the references cited above, the magnesium chloride solutions are processed by providing the solution to a thermal decomposition step, where the magnesium chloride reacts with water from the solution to form solid magnesium oxide and a gas stream comprising water and HCl.

Other processes for converting magnesium chloride to magnesium oxide have also been described.

EP25427 describes spray-drying of a magnesium chloride solution to form magnesium chloride dihydrate, and roasting the magnesium chloride dihydrate at 600° C. in a rotating oven.

U.S. Pat. No. 4,425,314 also describes conversion of magnesium chloride dihydrate to MgO at a temperature of 600-800° C. The magnesium chloride dihydrate is advantageously obtained by drying an aqueous magnesium chloride solution to form magnesium chloride hexahydrate, and converting the compound into the dihydrate.

DD28740 describes drying of a magnesium chloride solution to form magnesium chloride dihydrate, e.g. using a spray dryer. The magnesium chloride dihydrate is then contacted in a reaction chamber at a temperature of at least 800° C. with hot gas.

SUMMARY

While the conversion of magnesium chloride dihydrate into magnesium oxide is believed to form an improvement over the processing of magnesium chloride solutions in that a process of improved flexibility is obtained, it has been found that there is still need for an improved process, in particular a method which can be carried out at higher speed and at lower temperatures than the processes known in the art. The present invention provides such a process.

The invention pertains to a method for conversion of magnesium chloride into magnesium oxide and HCl, comprising the steps of
  providing a magnesium chloride compound to a thermohydrolysis reactor, the reactor being at a temperature of at least 300° C.,
  withdrawing MgO from the thermohydrolysis reactor in solid form, and withdrawing a HCl containing gas stream from the thermohydrolysis reactor, wherein the magnesium chloride compound provided to the thermohydrolysis reactor is a solid magnesium chloride compound which comprises at least 50 wt. % of $MgCl_2 \cdot 4H_2O$.

Surprisingly it has been found that by providing solid magnesium chloride compound which comprises at least 50 wt. % of $MgCl_2 \cdot 4H_2O$.hydrate as starting material for the thermohydrolysis, a process is obtained which is fast, can be carried out without blocking of the equipment, and can be operated in a manner which is efficient both as regards apparatus and energy. It can also be integrated in a process for converting a magnesium chloride solution.

The present invention will be discussed in more detail below.

BRIEF DESCRIPTION OF THE DRAWINGS

The invention will be illustrated by the following figures, without being limited thereto or there by.

DETAILED DESCRIPTION

Figure 1:
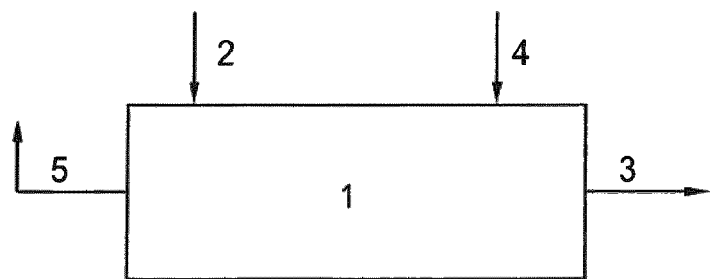
FIG. 1 illustrates a first embodiment of the present invention.

In the process according to the invention it has been found that the selection of $MgCl_2 \cdot 4H_2O$ as starting material gives attractive results. In contrast, other solid magnesium chloride compounds are less suitable for use as starting material for thermohydrolysis. More in particular, magnesium chloride anhydrate and magnesium chloride monohydrate have been found to require a long reaction time, higher reaction temperatures, and the presence of HCl. Magnesium chloride dihydrate also requires a relatively long reaction time and higher temperature. On the other hand, magnesium chloride hexahydrate has been found to melt, which results in blocking of the equipment.

In the process according to the invention, a solid magnesium chloride compound comprising at least 50 wt % of $MgCl_2.4H_2O$ is provided to a thermohydrolysis reactor.

It is preferred for the magnesium chloride compound to comprise less than 30 wt. % of magnesium chloride hexahydrate, in particular less than 20 wt. %, more in particular less than 10 wt. % and/or less than 40 wt. % of the total of magnesium chloride anhydrate and magnesium chloride monohydrate, preferably less than 30 wt. %, more preferably less than 20 wt. %, still more preferably less than 10 wt. %. It is also preferred for the magnesium chloride compound to comprise less than 40 wt. % of the total of magnesium chloride anhydrate, magnesium chloride monohydrate, and magnesium chloride dihydrate, preferably less than 30 wt. %, more preferably less than 20 wt. %, still more preferably less than 10 wt. %. Within this embodiment it is preferred to also meet the requirement on the percentage of magnesium chloride hexahydrate as specified above.

It is preferred for the magnesium chloride compound to consist for at least 60 wt. % of $MgCl_2.4H_2O$, in particular at least 80 wt. %, more in particular at least 90 wt. %. This is because $MgCl_2.4H_2O$ gives best results in the conversion into magnesium oxide, requiring lower conversion temperatures and shorter reaction times.

The composition of the magnesium chloride compound can be determined by methods known in the art, e.g., via XRD.

In the thermohydrolysis step, the magnesium chloride compound is heated to a temperature of at least 300° C. The process step is sometimes also indicated as the roasting step or thermal decomposition step. In the thermohydrolysis step magnesium chloride reacts with $H_2O$ to form MgO and HCl. MgO is withdrawn from the thermohydrolysis reactor in solid form. A HCl containing gas stream is also withdrawn from the thermohydrolysis reactor.

Thermal decomposition is conducted at a temperature of a least 300° C., which is the minimum temperature at which $MgCl_2$ decomposes. Preferably, thermal decomposition is conducted at a temperature of at least 400° C. Due to energy costs, the temperature is preferably below 1000° C., more preferably below 800° C., in particular below 700° C., more in particular below 600° C. It has been found that for magnesium chloride tetrahydrate as it is used in the present invention, a high degree of conversion can be obtained in a temperature range of 300-600° C. while still operating at reasonable throughput. Operating in a temperature range of 350-550° C., in particular 400-500° C. is considered preferred, as in this temperature range an optimum balance may be obtained between the energy considerations influencing the selection of the temperature and throughput considerations. The temperature mentioned is the temperature of the gas in the unit.

Thermal decomposition as applied in the present invention is preferably conducted at a pressure of 0.1-10 bar. However, the use of elevated pressure may be undesirable, because of an increased risk of corrosion due to the HCl not being able to condense. Preferably, thermal decomposition is conducted at atmospheric pressure, to avoid unnecessary energy costs and the need for expensive high pressure equipment.

In the thermal decomposition step, the magnesium chloride tetrahydrate is converted to MgO and HCl. The amount of water of hydration present in the magnesium chloride hydrate is sufficient to provide the oxygen and hydrogen required for stoichiometric conversion. Nevertheless, it may be preferred to add a small amount of water during the thermal decomposition step, as this may help to obtain complete conversion. Suitable amounts of water, if added are, e.g., 0.01-10 wt. %, calculated on the weight of the magnesium chloride compound.

The thermohydrolysis is generally carried out in the presence of a gas stream provided to the reactor, which can be used to provide heat to the system and withdraw HCl from the reactor. The nature of the gas stream is not critical. It can, e.g., be air or a combustion gas. The latter may be preferred because of its higher temperature.

In one embodiment the gas stream comprises 40-100 wt. % nitrogen gas, in particular 40-80 wt. % nitrogen, 0-15 wt. % of oxygen, and 0-20 wt. % of $CO_2$. Water can, e.g., be present in an amount of 5-20 wt. %. Obviously, the total of the composition will amount to 100 wt. %. A suitable gas can, e.g., be a gas stream resulting from a combustion step, e.g., the combustion of natural gas.

It has been found that the presence of HCl may help to ensure complete conversion within the time frame of the reaction. Not wishing to be bound by theory it is believed that the presence of HCl may help to prevent the formation of MgClOH, which has a low reactivity. As HCl is formed during the reaction, its beneficial presence can be profited from by leading the product gas over the magnesium chloride compound still to be converted. If so desired, it is possible to add additional HCl during the reaction.

The thermohydrolysis reactor may have any conventional size or shape, and may op operated in continuous mode or batch mode. Where applicable the gas stream can be co-current with the transport direction of the magnesium chloride compound or countercurrent with the transport direction of the magnesium chloride compound. In a preferred embodiment the direction of the gas stream is countercurrent to the transport direction of the magnesium chloride compound.

Suitable thermohydrolysis apparatus is known in the art, and include spray roasters and fluid bed roasters. In the present case, apparatus with a high degree of filling, e.g. 10-50 vol. %, calculated on the internal volume of the unit, can be used for example. An advantage of a relatively high degree of filling is that temperature and residence time can be controlled quite easily.

In one embodiment, the thermohydrolysis reactor is a tube reactor wherein the magnesium chloride compound enters the reactor at or near one end of the reactor, further indicated as the feed end, and product magnesium oxide is withdrawn at or near the other end of the reactor, further indicated as the product end, while a gas stream enters the reactor at or near the product end, and a gas stream comprising HCl is withdrawn at or near the feed end. This embodiment is preferred because it ensures that the product gas is led over the magnesium chloride compound still to be converted as explained above. It is also attractive because it allows an efficient use of energy. Further, tube reactors allow the use of a relatively high degree of filling, as indicated above.

As will be discussed in more detail below, the tube reactor will generally be provided with mixing means and/or transportation means.

This embodiment is illustrated in FIG. 1.

In FIG. 1, a tube reactor (1) is depicted, which is at elevated temperature through heating means (not shown). The magnesium chloride compound is provide to the reactor through line (2), where it is converted into magnesium oxide, which is withdrawn through line (3). The reactor may comprise transportation means (not shown) for the solid material. Suitable transportation means encompass rotating internal screws, paddles or discs, or a rotating wall. It is also possible for the reactor to be at an angle with the horizontal, with feed end being located higher than the product end. The reactor can also be vertical, or be provided with a moving bed.

A heated gas stream is provided to the reactor through line (4). The gas stream comes into contact with the solid material, i.e. magnesium chloride compounds and magnesium oxide, present in the reactor. The HCl generated during the conversion reaction is taken up by the gas stream, and a HCl containing product stream is removed through line (5). Suitable reactors are known in the art. They include, for example, a rotating kiln, a moving bed, or a screw conveyor. It is within the scope of the skilled person to select a suitable reactor configuration.

In this embodiment, the temperature of the gas stream provided to the unit will decrease over the unit due to heat transfer. It is preferred for the gas stream removed from the unit to have a temperature of at least 300° C., in particular at least 400° C. The maximum temperature may be at most 1000° C., in particular at most 800° C., more in particular at most 700° C., in some embodiments at most 600° C. A range of 350-550° C., in particular 400-500° C. may be preferred. The temperature of the gas stream as it enters the unit will be higher than the temperature as it leaves the unit. The exact entrance temperature will depend on the source of the gas stream and on the heat transfer properties of the unit. The entrance temperature may be, e.g., in the range of 700-1500° C., in particular 800-1500° C.

It has been found that the process according to the invention makes for efficient conversion of the magnesium chloride compound to magnesium oxide. This makes for low residence times. In one embodiment, the residence time in the reactor is at most 30 minutes, calculated from entrance of the magnesium chloride compound in the reactor to removal of the corresponding magnesium oxide from the reactor. Residence time may be lower, e.g., at most 20 minutes, or at most 15 minutes, or at most 10 minutes, or even less, e.g., at most 5 minutes.

Generally, the reaction time will be at least 15 seconds. The exact residence time will depend on the type of reactor and the process conditions. Residence time can be reduced by selecting a higher operating temperature, a smaller particle size, and providing additional water (steam) or HCl.

The starting material in the present invention is a solid magnesium chloride compound comprising at least 50 wt. % of $MgCl_2.4H_2O$. As indicated above it is preferred for the magnesium chloride compound to consists for at least 60 wt. % of $MgCl_2.4H_2O$, in particular at least 80 wt. %, more in particular at least 90 wt. %.

The magnesium chloride compound comprising at least 50 wt. % of $MgCl_2.4H_2O$ can be obtained by drying a magnesium chloride solution under controlled conditions, namely at a temperature of 100-160° C. If the drying is carried out at a temperature below 100° C., magnesium chloride hexahydrate, the presence of which will detrimentally affect the convention step to MgO, will be formed in too high amounts. For this reason it may be preferred for the drying to be carried out at a temperature of at least 110° C., in particular at least 120° C. On the other hand, if the drying is carried out at a temperature of above 160° C., magnesium chloride anhydrate, magnesium chloride monohydrate, and magnesium chloride dihydrate, the presence of which will detrimentally affect the convention step to MgO, will be formed in too high amounts. It may be preferred to carry out drying at a temperature of at most 140° C.

It may be preferred for the drying step to be carried out at a temperature of 110-160° C., more specifically 120-160° C. The preference for this temperature range is triggered by the desire to form magnesium chloride tetrahydrate and by energy considerations. It is within the scope of the skilled person to select a suitable drying temperature. It is noted that the temperature for the drying step as specified here is the temperature in the dryer.

The concentration of the magnesium chloride starting solution is not critical, and may depend on what is available. As a general range a value of 5-45 wt. % may be mentioned. It may be preferred for the magnesium chloride concentration to be relatively high, e.g., in the range of 20-45 wt. %, more particular in the range of 30-45 wt. %. The use of more concentrated solutions is accompanied by less water removal, which is attractive from an economic point of view. Further advantages of the use of higher concentrations in specific embodiments will be discussed below.

The drying step can be carried out by methods known in the art. Spray-drying is suitable, both from a practical point of view and from an economic point of view. Other methods like fluidized bed drying can also be used. It is within the scope of the skilled person to determine suitable drying methods.

In one embodiment, the drying step is carried out in the presence of a HCl-containing gas stream. This will be the case where a HCl-containing gas stream derived from the thermohydrolysis step is provided to the drying step. This is particularly attractive, because the gas stream is derived from the thermohydrolysis step at a high temperature, e.g., of at least 300° C., in particular at least 400° C., and the high temperature can be used to evaporate water. It may be preferred for the gas stream to be at most 1000° C., in particular at most 800° C., more in particular at most 700° C., in some embodiments at most 600° C. A range of 350-550° C., in particular 400-500° C. may be preferred. It is noted that where a gas stream with a temperature in this range is used in spray drying, its temperature will immediately be reduced to a lower value, in particular a value within the range of 100-160° C., due to the evaporation of water. In the case of a spray dryer, the drying temperature in the unit, which is important for the formation of the desired type of magnesium chloride hydrate as is discussed above, is dependent on the temperature of the entrance gas and on the concentration of the magnesium chloride solution, which determines the amount of water to be evaporated. By regulating the temperature of the spray drying gas and the concentration of the magnesium chloride solution, the drying temperature within the unit can be set at the desired value.

In one embodiment, the present invention pertains to an integrated process for converting a magnesium chloride solution into magnesium oxide and HCl, which process comprises the steps of subjecting a magnesium chloride solution to a drying step at a temperature of 100-160° C., in particular 120-160° C. to form a magnesium chloride compound comprising at least 50 wt. % of $MgCl_2.4H_2O$, providing said magnesium chloride compound to a thermohydrolysis reactor, the reactor being at a temperature of at least 300° C., and withdrawing MgO from the thermohydrolysis reactor in solid form, and withdrawing a HCl containing gas stream from the thermohydrolysis reactor.

In a preferred embodiment, the drying step is a spray drying step, and the HCl containing gas stream withdrawn from the thermohydrolysis reactor is provided to the spray drying step to be combined with the magnesium chloride solution. This will be discussed in more detail below.

The descriptions of the various aspects of the individual steps as given above also apply to the integrated process.

Figure 2:
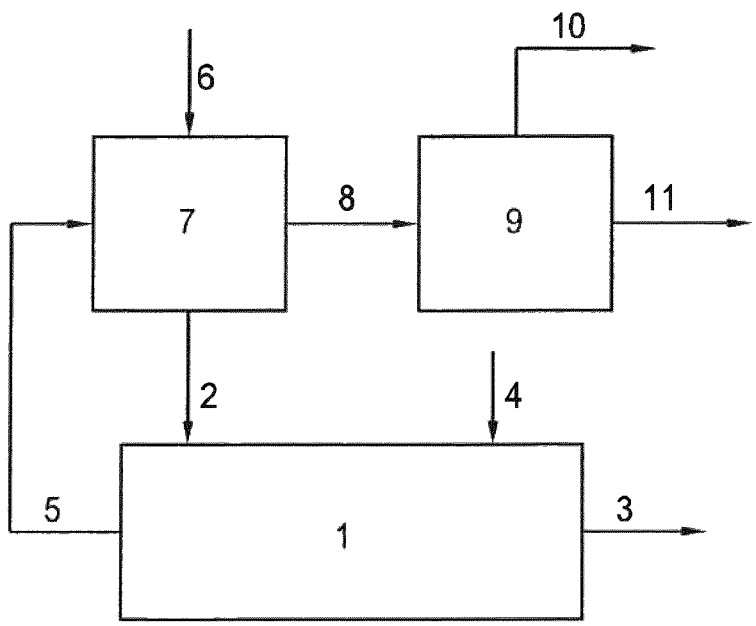
FIG. 2 illustrates a second embodiment of the present invention, wherein the step of converting a specific magnesium chloride compound to magnesium oxide and HCl is combined with a step of manufacturing the specific magnesium chloride compound from a magnesium chloride solution.

One embodiment of the integrated process is illustrated in FIG. 2.

In FIG. 2, line (6) provides a magnesium chloride solution to a dryer (7). In dryer (7), a solid magnesium chloride compound is formed, which is provided through line (2) to thermohydrolysis reactor (1). In reactor (1) the magnesium chloride compound is converted into magnesium oxide, which is withdrawn through line (3). A heated gas stream is provided to the reactor through line (4). The gas stream comes into contact with the solid material, i.e. magnesium chloride compounds and magnesium oxide, present in the reactor. The HCl generated during the conversion reaction is taken up by the gas stream, and a HCl containing product stream is removed through line (5). In the embodiment presented in FIG. (2) the HCl containing gas stream is provided to dryer (7), where the heat in the gas is used in the drying. The dryer (7) generates an off gas, which is withdrawn through line (8). At least in the case that the effluent stream (5) from reactor (1) is provided to dryer (7), the off gas from dryer (7) contains HCl, generally in an amount of 5-30 wt. %, in particular 15 to 30 wt. %, more in particular 20-25 wt. %. The further composition of the off gas is not critical. It will depend on the gas provided to reactor (1) through line (4). It will generally comprise nitrogen and optionally one or more of oxygen, $CO_2$, and further compounds.

The offgas may be processed as desired. In one embodiment, as depicted in FIG. 2, the offgas is provided to an absorber (9), where it is contacted with water which absorbs the HCl to form a solution of HCl in water. Depending on the concentration of HCl in the off gas, the HCl solution may have a concentration of 10-30 wt. %, in particular 15-30 wt. %, more in particular 20-25 wt. %. These high concentration ranges can in particular be obtained where a magnesium chloride solution with a relatively high concentration is used as starting material for the drying step. This is a further reason why the use of such more concentrated solutions is considered preferred. That fraction of the offgas from the dryer (7) not absorbed in the absorber (9) is depicted as (11).

As indicated earlier, the process according to the invention is particularly suitable for incorporation into a method for manufacturing organic components, in particular carboxylic acids using a fermentation step.

In one embodiment the present invention therefore pertains to a process comprising the steps of
  subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate,
  subjecting the magnesium carboxylate to an acidification step wherein the magnesium carboxylate is contacted with HCl in an aqueous environment to form an aqueous mixture comprising carboxylic acid and magnesium chloride,
  subjecting the aqueous mixture comprising carboxylic acid and magnesium chloride to a separation step, to form an effluent comprising carboxylic acid and a magnesium chloride solution,
  subjecting the magnesium chloride solution to a drying step at a temperature of 100-160° C., in particular 120-160° C., to form a magnesium chloride compound comprising at least 50 wt. % of $MgCl_2.4H_2O$,
  providing said magnesium chloride compound to a thermohydrolysis reactor, the reactor being at a temperature of at least 300° C.,
  withdrawing MgO from the thermohydrolysis reactor in solid form,
  withdrawing a HCl containing gas stream from the thermohydrolysis reactor.

In a preferred embodiment of this integrated process, the magnesium oxide withdrawn from the thermohydrolysis reactor is recycled at least in part to the fermentation step. This can be done in the form of MgO or after conversion into magnesium hydroxide, e.g., by contacting the magnesium oxide with water to obtain a magnesium hydroxide slurry.

In a preferred embodiment of the integrated process, the HCl-containing gas stream derived from the drying step is recycled at least in part to the acidification step. In one embodiment the HCl-containing gas stream is converted to a HCl solution by absorbing it in water, and the solution is recycled to the acidification step. In another embodiment, the HCl-containing gas stream is provided to the acidification step in gaseous form.

It is particularly preferred for the integrated process according to the invention to encompass a combination of the MgO recycling and the HCl recycling described above.

The specific embodiments and preferences described above for the process according to the invention also apply to the integrated process.

The various steps in the integrated process which are additional to the processing of the magnesium chloride solution will be discussed below.

In the first step a carbon source is subjected to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium carboxylate, biomass, and optionally further components such as impurities like are sugars, proteins, and salts.

If so desired, the fermentation broth may be subjected to a biomass removal step, e.g., a filtration step, before further processing. This is generally preferred for improving product quality. Depending on the carboxylic acid produced, another intermediate step may be separation of solid reaction product, e.g., magnesium carboxylate, from the fermentation broth, before, after, or simultaneous with biomass removal, and optionally subjecting the magnesium carboxylate to a washing step.

Depending on the carboxylic acid produced, another intermediate step may be subjecting the fermentation broth to a concentration step to increase the concentration of magnesium carboxylate in the composition before acidification. This step may be carried out before, after, or simultaneous with biomass removal.

Other intermediate steps, e.g., purification steps, may be carried out as desired, as will be evident to the skilled person.

The next step in the integrated process according to the invention is subjecting the magnesium carboxylate to an acidification step, also sometimes indicated as acidulation step, wherein the magnesium carboxylate is contacted with HCl in an aqueous environment to form an aqueous mixture comprising carboxylic acid and magnesium chloride.

There are various ways in which this step can be effected. The acidulation step is typically conducted by bringing the carboxylate salt in contact with an acidic HCl solution. However, in some embodiments it may also be possible to contact the carboxylate salt with gaseous HCl.

The carboxylate salt may be in solid and/or dissolved form. In one embodiment, the carboxylate salt is provided in solid form. In this case, the acidulation step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25%, up to, e.g. 50 wt. %, or e.g. 40 wt. %.

The carboxylate salt may also be in dissolved form, typically as part of an aqueous solution. In this case, the acidulation step can be conducted by bringing the carboxylate salt in contact with an acidic solution or an acidic gas.

The acidulation step may also be conducted on a mixture of carboxylic acid and carboxylate salt. Such a mixture may for example be obtained in a low pH fermentation. The mixture may for example be an aqueous suspension.

When acidulation of the carboxylate salt is conducted by contacting it with an acidic HCl solution, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution.

Acidulation is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a carboxylate solution or suspension. In particular, HCl gas may be blown through the solution or suspension.

Preferably, acidulation is conducted at a temperature of 75° C. or less. At higher temperatures, it becomes uneconomical to adapt equipment to the harsh conditions of an acidic environment at high temperatures.

The acidification step results in the formation of an aqueous liquid comprising carboxylic acid and magnesium chloride. This aqueous liquid is subjected to a separation step, optionally after intermediate processing steps have been carried out such as a concentration step.

Suitable separation steps are known in the art. The nature of the step to be used depends on the nature and property of the acids.

Where the carboxylic acid is present in whole or in part as solid in the aqueous liquid, separation can take place using conventional solid-liquid separation methods such as filtration, centrifugation, etc.

Where the carboxylic acid is present in whole or in part as a separate organic phase in the aqueous liquid, separation can take place using conventional liquid-liquid separation methods, e.g., decantation, settling, centrifugation, use of plate separators, use of coalescers, and use of hydrocyclones. An extractant may be added to improve the separation efficiency. Combination of different methods and apparatus may also be used.

Where the carboxylic acid is present dissolved in the aqueous liquid, separation can take place using, e.g., extraction with a suitable extractant.

The nature of the carboxylic acid manufactured is not critical to the intergrated process according to the invention.

In one embodiment the carboxylic acid is a mono-, di- or tri-carboxylic acid comprising at least 2, but no more than 6 carbon atoms (C2-6 carboxylic acid). In one embodiment, the carboxylic acid is selected from the group consisting of lactic acid, succinic acid, propionic acid, 3-hydroxypropionic acid, 2-, 3-, and 4-hydroxybutyric acid, citric acid, fumaric acid, itaconic acid, adipic acid, acrylic acid, levulinic acid, maleic acid, 2,5-furandicarboxylic acid, mandelic acid, malic acrid, and tartartic acid. Preferably, the carboxylic acid is selected from the group consisting of lactic acid, succinic acid, propionic acid, 3-hydroxypropionic acid, 2-, 3-, and 4-hydroxybutyric acid and citric acid.

In one embodiment, the carboxylic acid is selected from the mono-carboxylic acids with 2-6 carbon atoms. In one embodiment, the monocarboxylic acid with 2-6 carbon atoms does not contain hydroxyl-groups. Within this group, examples of suitable acids are propionic acid, acrylic acid, butyric acid, and valeric acid.

In another embodiment, the monocarboxylic acid contains at least one hydroxyl-group. Within this group, in one embodiment it may be preferred to select the acid from the group of lactic acid, glycolic acid, 3-hydroxypropionic acid, 2-, 3-, and 4-hydroxybutyric acid. In another embodiment within this group it may be preferred to select the acid from the group of glycolic acid, 3-hydroxypropionic acid, and 2-, 3-, and 4-hydroxybutyric acid. In a further embodiment it may be preferred for the acid to be lactic acid.

In another embodiment, the carboxylic acid is a polycarboxylic acid, more in particular a di- or tri-carboxylic acid comprising at least 2, but no more than 6 carbon atoms (C2-6 carboxylic acid). In one embodiment, the polycarboxylic acid is selected from the group consisting of succinic acid, citric acid, fumaric acid, itaconic acid, adipic acid, maleic acid, 2,5-furandicarboxylic acid, mandelic acid, malic acid, and tartartic acid. Preferably, the polycarboxylic acid is selected from the group consisting of succinic acid, citric acid, fumaric acid, itaconic acid, adipic acid, and 2,5-furandicarboxylic acid. The polycarboxylic acid may in particular be selected from succinic acid, fumaric acid, itaconic acid, and 2,5-furandicarboxylic acid.

Figure 3:
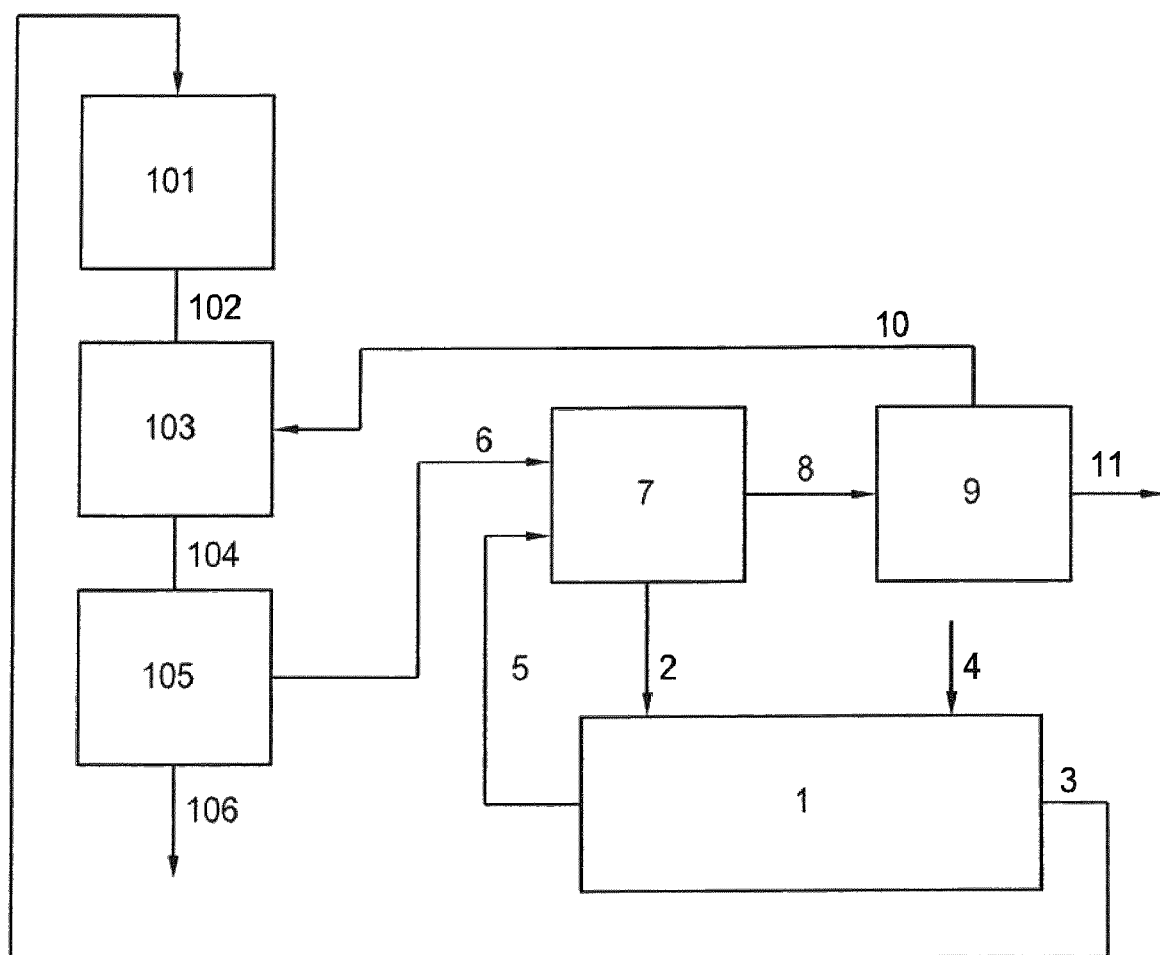
FIG. 3 illustrates a third embodiment of the present invention, wherein the process of FIG. 2 is integrated into a fermentation process.

FIG. 3 illustrates an embodiment of the integrated process according to the invention. In FIG. 3, a fermentation step is carried out in fermentation reactor (101), which is provided with a carbon source and optionally further components such as nutrients through lines not shown. In the fermentation step a carbon source is fermented by means of a micro-organism in a fermentation broth to form carboxylic acid and neutralizing at least part of the carboxylic acid by adding a magnesium base, thereby obtaining a magnesium carboxylate. The magnesium base is added through line (3). The magnesium base is derived from MgO generated in the thermal decomposition step. The MgO may be provided as such, or after having been slurried in an aqueous liquid or converted to magnesium hydroxide in steps not shown.

The fermentation broth comprising a magnesium carboxylate salt is provided to an acidification step (103) through line (102). Intermediate steps such as biomass removal or concentration may be carried out, but are not shown. In the acidification step (103) the magnesium carboxylate is contacted with HCl in an aqueous environment to form an aqueous mixture comprising carboxylic acid and magnesium chloride. The HCl is provided through line (10) and is derived from the drying step in the dryer (7). In the embodiment presented in FIG. 3, the HCl-containing gas stream derived from dryer (7) is provided through line (8) to an absorber (9), where the HCl is adsorbed in water to form a HCl solution, which is provided through line (10) to the acidification step (103). It is also possible to provide the HCl-containing gas stream (8) directly to acidification step (103). That fraction of the HCl-containing gas stream from the dryer (7) not absorbed in the absorber (9) is depicted as (11).

The aqueous mixture comprising carboxylic acid and magnesium chloride is provided to a separation step (105) through line (104). The separation step may be carried out as described above. Where separation step (105) makes use of an extractant, this is provided through lines not shown. Separation step (105) results in an effluent comprising carboxylic acid and a magnesium chloride solution. The product carboxylic acid is withdrawn through line (106). The magnesium chloride solution is withdrawn through line (6), and processed further as described above in the context of FIG. (2).

As will be evident to the skilled person, the various aspects of the thermohydrolysis step are also applicable where this step is incorporated into a process for conversion of a magnesium chloride solution. The various aspects of the process for conversion of a magnesium chloride solution are also applicable where this process is incorporated into an integrated fermentation process.

The present invention is elucidated by the following examples, without being limited thereto or thereby.

Examples

Starting materials were prepared as follows:

$MgCl_2.6H_2O$: Magnesium chloride hexahydrate was obtained commercially.

$MgCl_2.4H_2O$: Magnesium chloride tetrahydrate was obtained by placing magnesium chloride hexahydrate in an oven at 130° C. for 24 hours. The weight reduction of the sample was measured, confirming the formation of magnesium chloride tetrahydrate.

$MgCl_2.2H_2O$: Magnesium chloride dihydrate was created by spray-drying a magnesium chloride solution at 140° C. TGA measurements confirmed that the magnesium chloride compound contained at least 80 wt. % of magnesium chloride dihydrate.

$MgCl_2$: Anhydrous magnesium chloride was obtained commercially.

The samples were tested as follows:

A small amount of solid material is placed in a quartz glass crucible with a porous metal disc as base. The arrangement of material in the container with the porous metal base in placed in a glass tube connected to a burner. Using a suction pump hot gases from the burner are displaced through the sample. A temperature sensor is placed inside the sample to record the temperature, and the temperature is controlled by controlling the flow delivered by the suction pump.

For each material a set of experiments was carried out at 500° C. and 600° C. Samples were taken after specified periods of time, and the conversion into magnesium oxide determined. The results are presented in tables 1 and 2.

TABLE 1

Thermal decomposition at 500° C. - degree of conversion

| Species | Time (minutes) | | | |
|---|---|---|---|---|
| | 2 | 5 | 10 | 15 |
| $MgCl_2.6H_2O$ | | Melts | | |
| $MgCl_2.4H_2O$ | 0.3 | 0.8 | 0.8 | 0.8 |
| $MgCl_2.2H_2O$ | 0.4 | 0.4 | 0.4 | 0.4 |
| $MgCl_2$ | 0 | 0 | 0 | 0 |

TABLE 2

Thermal decomposition at 600° C. - degree of conversion

| Species | Time (minutes) | | | |
|---|---|---|---|---|
| | 2 | 5 | 10 | 15 |
| $MgCl_2.6H_2O$ | | Melts | | |
| $MgCl_2.4H_2O$ | 0.95 | 1 | 1 | 1 |
| $MgCl_2.2H_2O$ | 0.9 | 0.95 | 0.95 | 0.95 |
| $MgCl_2$ | 0.15 | 0.15 | 0.15 | 0.15 |

As can be seen from the above tables, $MgCl_2.6H_2O$ melts, both at 500° C. and at 600° C. $MgCl_2$ does not show any conversion into MgO under these reaction conditions in this time frame. $MgCl_2.4H_2O$ and $MgCl_2.2H_2O$ both show substantial conversion into MgO. At 500° C. $MgCl_2.4H_2O$ shows a conversion of 80% after 10 minutes, and at 600° C., a conversion of 95% is already obtained after 2 minutes, with 100% conversion being obtained after 5 minutes. For $MgCl_2.2H_2O$ the conversion is slower, both at 500° C. and at 600° C. This illustrates that $MgCl_2.4H_2O$ shows faster conversion at lower reaction temperatures than $MgCl_2.2H_2O$.

The invention claimed is:

1. Method for conversion of magnesium chloride into magnesium oxide and HCl, said method comprising the steps of:
    providing a magnesium chloride compound to a thermohydrolysis reactor, the reactor being at a temperature of at least 300° C.; and,
    withdrawing MgO from the thermohydrolysis reactor in solid form, and withdrawing an HCl containing gas stream from the thermohydrolysis reactor,
    wherein the magnesium chloride compound provided to the thermohydrolysis reactor is a solid magnesium chloride compound which comprises at least 60 wt. % of $MgCl_2.4H_2O$.

2. The method according to claim 1, wherein at least 80 wt. % of the magnesium chloride compound is $MgCl_2.4H_2O$.

3. The method according to claim 1, wherein the magnesium chloride compound comprises less than 30 wt. % of magnesium chloride hexahydrate.

4. The method according to claim 1, wherein the magnesium chloride compound comprises less than 40 wt. % of the total of magnesium chloride anhydrate, magnesium chloride monohydrate and magnesium chloride dihydrate.

5. The method according to claim 4, wherein the magnesium chloride compound comprises less than 30 wt. % of the total of magnesium chloride anhydrate, magnesium chloride monohydrate and magnesium chloride dihydrate.

6. The method according to claim 1, wherein the magnesium chloride compound comprises less than 30 wt. % of magnesium chloride hexahydrate and less than 40 wt. % of the total of magnesium chloride anhydrate, magnesium chloride monohydrate and magnesium chloride dihydrate.

7. The method according to claim 1, said magnesium chloride compound comprising at least 60 wt. % of $MgCl_2.4H_2O$ is obtained by subjecting a magnesium chloride solution to a drying step at a temperature of 100-160° C.

8. The method according to claim 1, wherein the thermohydrolysis reactor is at a temperature below 800° C.

9. The method according to claim 1, wherein the thermohydrolysis is carried out in the presence of a gas stream provided to the thermohydrolysis reactor.

10. The method according to claim 9, wherein the provided gas stream provides heat to the thermohydrolysis reactor and carries HCl from the thermohydrolysis reactor.

11. The method according to claim 1, wherein the thermohydrolysis reactor is a tube reactor wherein the magnesium chloride compound enters the reactor at or near one end of the reactor, further indicated as the feed end, and product magnesium oxide is withdrawn at or near the other end of the reactor, further indicated as the product end, while a gas stream enters the reactor at or near the product end, and a gas stream comprising HCl is withdrawn at or near the feed end.

12. A method for conversion of magnesium chloride into magnesium oxide and HCl, said method comprising the steps of:
   a) subjecting a magnesium chloride solution to a drying step at a temperature of 100-160° C. to form a magnesium chloride compound comprising at least 50 wt. % of $MgCl_2.4H_2O$;
   b) providing said magnesium chloride compound to a thermohydrolysis reactor, the reactor being at a temperature of at least 300° C.; and,
   c) withdrawing MgO from the thermohydrolysis reactor in solid form, and withdrawing an HCl containing gas stream from the thermohydrolysis reactor,
   wherein the drying step a) is carried out in the presence of HCl.

13. The method according to claim 12, wherein said drying step a) forms a magnesium chloride compound comprising at least 60 wt. % of $MgCl_2.4H_2O$.

14. The method according to claim 12, wherein said drying step a) forms a magnesium chloride compound comprising less than 40 wt. % of the total of magnesium chloride anhydrate, magnesium chloride monohydrate and magnesium chloride dihydrate.

15. The method according to claim 12, wherein the drying step a) is carried out at a temperature of 110-160° C.

16. The method according to claim 12, wherein the HCl present in the drying step a) is provided by providing the HCl-containing gas stream derived from the thermohydrolysis reactor to the drying step.

17. The method according to claim 12, wherein the drying step a) is performed by spray-drying.

18. The method according to claim 12, wherein the thermohydrolysis is carried out in the presence of a gas stream provided to the thermohydrolysis reactor.

19. The method according to claim 12, wherein the provided gas stream provides heat to the thermohydrolysis reactor and carries HCl from the thermohydrolysis reactor.

20. The method according to claim 12 further comprising the steps of:
   subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate;
   subjecting the magnesium carboxylate to an acidification step wherein the magnesium carboxylate is contacted with HCl in an aqueous environment to form an aqueous mixture comprising carboxylic acid and magnesium chloride; and,
   subjecting the aqueous mixture comprising carboxylic acid and magnesium chloride to a separation step, to form an effluent comprising carboxylic acid and a magnesium chloride solution, said magnesium chloride solution being provided to drying step a).

21. The method according to claim 20 comprising the step of recycling the magnesium oxide withdrawn from the thermohydrolysis reactor at least in part to the fermentation step.

22. A method for conversion of magnesium chloride into magnesium oxide and HCl, said method comprising the steps of:
   a) subjecting a magnesium chloride solution to a drying step at a temperature of 100-160° C. to form a magnesium chloride compound comprising at least 50 wt. % of $MgCl_2.4H_2O$;
   b) providing said magnesium chloride compound to a thermohydrolysis reactor, the reactor being at a temperature of at least 300° C.; and,
   c) withdrawing MgO from the thermohydrolysis reactor in solid form, and withdrawing an HCl containing gas stream from the thermohydrolysis reactor,
   wherein the drying step a) is performed by spray-drying.

23. The method according to claim 22, wherein said drying step a) forms a magnesium chloride compound comprising at least 60 wt. % of $MgCl_2.4H_2O$.

24. The method according to claim 22, wherein said drying step a) forms a magnesium chloride compound comprising less than 40 wt. % of the total of magnesium chloride anhydrate, magnesium chloride monohydrate and magnesium chloride dihydrate.

25. The method according to claim 22, wherein the drying step a) is carried out at a temperature of 110-160° C.

26. The method according to claim 22, wherein the drying step a) is carried out at a temperature of 120-160° C.

27. The method according to claim 22, wherein the thermohydrolysis is carried out in the presence of a gas stream provided to the thermohydrolysis reactor.

28. The method according to claim 22, wherein the provided gas stream provides heat to the thermohydrolysis reactor and carries HCl from the thermohydrolysis reactor.

29. The method according to claim 22 further comprising the steps of:
   subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate;

subjecting the magnesium carboxylate to an acidification step wherein the magnesium carboxylate is contacted with HCl in an aqueous environment to form an aqueous mixture comprising carboxylic acid and magnesium chloride; and, subjecting the aqueous mixture comprising carboxylic acid and magnesium chloride to a separation step, to form an effluent comprising carboxylic acid and a magnesium chloride solution, said magnesium chloride solution being provided to drying step a).

30. The method according to claim 29 comprising the step of recycling the magnesium oxide withdrawn from the thermohydrolysis reactor at least in part to the fermentation step.

\* \* \* \* \*